United States Patent [19]
Lee et al.

[11] Patent Number: 5,422,261
[45] Date of Patent: Jun. 6, 1995

[54] COMPOSITION CONTAINING COLLAGENASE AND CHYMOPAPAIN FOR HYDROLYZING CONNECTIVE TISSUE TO ISOLATE CELLS

[75] Inventors: Catherine T. Lee, Laguna Hills; Cynthia Hornacek, Trabuco cyn; Tan T. Dinh, Garden Grove, all of Calif.

[73] Assignee: Baxter International Inc., Deerfield, Ill.

[21] Appl. No.: 49,015

[22] Filed: Apr. 16, 1993

[51] Int. Cl.⁶ .......................... C12N 9/50; C12N 9/48; C12N 5/00; A61K 37/62
[52] U.S. Cl. .................................. 435/219; 435/212; 435/240.1; 424/94.2; 424/94.65; 424/94.67
[58] Field of Search ............ 435/220, 219, 212, 240.1; 424/94.2, 94.65, 94.67

[56] References Cited

U.S. PATENT DOCUMENTS

| | | | |
|---|---|---|---|
| 3,558,433 | 1/1971 | Stern | 435/219 |
| 4,142,999 | 3/1979 | Bloching et al. | 252/544 |
| 4,167,447 | 9/1979 | Masri et al. | 435/178 |
| 4,212,945 | 7/1980 | Nonaka | 435/212 |
| 4,212,946 | 7/1980 | Nonaka | 435/212 |
| 4,374,926 | 2/1983 | Stern | 435/23 |
| 4,439,423 | 3/1984 | Smith | 424/94.65 |
| 4,719,108 | 1/1988 | Smith | 424/94.2 |
| 4,812,314 | 3/1989 | Barenholz | 424/450 |
| 4,978,332 | 12/1990 | Luck | 604/19 |
| 5,116,615 | 5/1992 | Gokcen | 424/94.2 |
| 5,227,157 | 7/1993 | McGinity et al. | 424/78.02 |

FOREIGN PATENT DOCUMENTS

| | | |
|---|---|---|
| 2474052 | 1/1980 | France . |
| 3713197A | 4/1987 | Germany . |
| 2064543 | 6/1981 | United Kingdom . |
| 89/10960 | 11/1989 | WIPO . |
| 91/14447 | 10/1991 | WIPO . |

OTHER PUBLICATIONS

C. C. Worthington, ed., "enzymes and related biochemicals", *Worthington Enzyme Manual*, 1988, pp. 93–95.
M. Maeda, "Studies on the characteristics of human lung mast cells . . . " *Okayama Igakkai Zasshi*, 1986, 98(5–6), pp. 475–486.
I. Marayuma et al., "Preparation of Single Smooth Muscle Cells . . . Collagenase and Papain", *J. Pharmacol. Methods*, Sep. 1987, 18(2), pp. 151–161.
B. J. Bolzon & D. W. Cheung, "Isolation and Characterization of Vascular Smooth Muscle Cells . . . ", *Hypertension*, Aug. 1989, pp. 137–144.
I. Maruyama et al., "Improvement of a Procedure . . . Collagenase and Papain", *J. Pharmacol. Methods*, 1988, 19(2), pp. 155–164.
E. Lammel et al., "Suppression of Steady Membrane Currents by Acetylcholine in Single Smooth Muscle Cells . . . ", *J. Physiol.*, 1991, 432, pp. 259–282.
K. Momose, "Isolation, configuration and contractile responses of single smooth muscle cells", *Nippon Yakurigaku Zasshi*, Mar. 1993, 101(3), pp. 101–110.
Tavakol, K. et al. "Enhanced dissolution of nucleus pulposus: Combined enzyme approach" *Surgical Forum (USA)*, 1986, vol. 37 pp. 491–494.

*Primary Examiner*—David M. Naff
*Assistant Examiner*—Mike Meller
*Attorney, Agent, or Firm*—Poms Smith Lande & Rose; Debra Condino

[57] ABSTRACT

Proteolytic enzyme compositions and processes for digesting connective tissue are disclosed. The enzyme compositions include collagenase, which is essentially free of toxins and non-collagen specific components, and chymopapain, which is essentially free of toxins. The enzyme compositions are used for dissociating microvessel cells from connective tissue. Recovered microvessel cells are incorporated into artificial vessel grafts. The enzyme compositions preferably contain an aqueous mixture of collagenase having an activity of about 43 nkat/ml to about 51 nkat/ml, and chymopapain having an activity of about 0.22 nkat/ml to about 0.44 nkat/ml.

4 Claims, 3 Drawing Sheets

Fig. 2

COMPOSITION CONTAINING COLLAGENASE AND CHYMOPAPAIN FOR HYDROLYZING CONNECTIVE TISSUE TO ISOLATE CELLS

BACKGROUND OF THE INVENTION

1. Field of the Invention

The present invention relates generally to proteolytic enzyme compositions and procedures for digesting connective tissue. More particularly, the present invention is directed to proteolytic enzyme compositions which reliably and reproducibly digest connective tissues in a variety of procedures including therapeutic applications and related cell dissociation and cell isolation techniques.

2. Description of Relevant Art

Proteolytic enzymes have found wide utility in a variety of laboratory and clinical applications. Typically these applications involve cell dissociation and related therapeutic procedures which are benefitted by the ability of proteolytic enzymes to hydrolytically break-up or loosen connective tissue networks. For example, bacterial collagenase derived from *Clostridium histolyticum* has been used to disperse cells in laboratory tissue culture applications. Additionally, collagenase has demonstrated utility in cell isolation procedures such as those associated with isolating pancreatic islets and dispersing a variety of tumor cells. Other uses for collagenase involve its topical use in clinical applications in which collagenase compositions are applied in the treatment of burns or ulcers and wound healing. Other uses include the treatment of Peyronie's disease and as an adjunct to cryoprostatectomy for the removal of retained cryoslough, intervertebral discolysis, and in ophthalmic surgery.

Like collagenase, chymopapain, the major proteolytic component of the crude latex of *Carica papaya*, has been utilized in the treatment of abnormal or herniated discs to selectively dissolve the nucleus pulposus of the disc. Other uses associated with chymopapain include its utility in cryosurgical healing processes.

Combinations of proteolytic enzymes such as compositions of bacterial collagenase and hyaluronidase are reportedly particularly useful for digesting or dissolving prostatic tissue in the treatment of benign prostatic hypertrophy. The combination of these two proteolytic enzymes apparently dissolves prostatic tissue in order to relieve the obstructive symptoms of prostatic hypertrophy.

Recently, bacterial collagenase derived from *Clostridium histolyticum* has found utility in procedures involving the dissociation and isolation of microvessel cells embedded in fatty tissues. These procedures generally involve combining fatty tissues having embedded microvessels, such as liposuctioned fat, with collagenase under conditions which cause the collagenase to disrupt and digest the connective tissue. By carefully separating the cells from the digested tissue, viable microvessel cells are recovered.

These viable and intact microvessel cells have found particular utility as a coating on the interior of synthetic small diameter vascular grafts implanted in humans and animals to replace blood vessels. Similarly, microvessel cells are useful as deposits on the surface of biomedical implant devices in general where they provide an improved biocompatibility to the implant. Apparently the microvessel cells contribute to the prevention of protein deposits and related cellular deposits on the implants which are known to occur when foreign materials are placed in contact with blood and tissue. In the case of vascular grafts these deposits can quickly cause the vessel to occlude, resulting in the functional failure of the graft.

One problem associated with the use of commercial sources of crude collagenase to digest fatty tissues, as well as connective tissue in general, is that the degree to which tissue digests or hydrolyzes is unpredictable. Moreover, cells which are isolated from tissue digestion procedures utilizing crude collagenase can be inferior in quality and have a low degree of viability and efficacy. Even when viable cells are successfully isolated, the yield and degree of viability is unpredictable.

The unpredictable nature of these procedures may be attributed to the lot variations inherent in commercial sources of crude collagenase. Another factor which may contribute to the lack of reproducibility in these procedures is the nature of the mixture of tissues being digested. While connective tissues are formed largely of collagen, for which collagenase is specific in its hydrolytic activity, significant amounts of other proteins and glycoproteins are additionally found in connective tissue matrices. Thus, collagenase alone may not effectively hydrolyze all of the tissue mixtures.

Further, collagenase derived from native bacteria differs widely in its collagen specific hydrolytic activity and the amount and character of impurities, including other proteases and toxins. The protease impurities in crude collagenase contribute to the hydrolysis of minor proteins in connective tissue and actually aid in the digestive process. However, unfortunately protease impurities are active with proteins generally and will react with collagenase, causing the crude collagenase to be subject to catalytic degradation. The toxin impurities associated with crude collagenase can be a serious problem for procedures involving both in vivo and in vitro applications. Toxins can disrupt cell membranes, destroy cell viability and generally lower cell yield. Additionally, impurities can contain variable amounts of bacterial DNA, which may cause cell damage and possible immunological problems when isolated cells or tissue digestion procedures involve in vivo applications. Finally, the noncollagenase impurities found in crude collagenase may act as sensitizing antigens which can cause anaphylactic shock if administered to patients.

Thus, in view of the varying and unpredictable nature of crude collagenase compositions which contain a host of proteolytically active and unreactive compounds as well as toxins, the use of crude collagenase compositions for therapeutic digestion procedures and cell dissociation techniques can be unreliable. Alternatively, using purified collagenase having essentially only collagen specific hydrolytic reactive components in these tissue digestion procedures has not been successful. The failure of purified collagenase in these procedures is apparently due to the tissue containing noncollagen proteins which are not digested by collagen specific collagenase. Crude collagenase will digest these tissues because it contains other proteolytic enzymes. However, it does so to a varying and unpredictable degree.

It has been suggested that bacteria genetically engineered to produce limited forms of collagenase having known molecular weights and hydrolytic activity may be advantageous when utilized in tissue digestion procedures. However, even when a wide range of isomeric forms of collagenase are utilized in tissue digestion procedures, the narrow specificity of collagenase in general precludes effectively hydrolyzing all of the tissue. This is because the wide spectrum of proteolytic activity and noncollagen specificity supplied by crude collagenase derived from native bacteria is not available in these genetically engineered sources of collagenase. Even when toxins are removed from genetically engineered sources of collagenase, the resulting collagenase compositions do not provide hydrolytic characteristics suitable for efficacious tissue digestion and/or cell dissociation procedures.

Accordingly, it is an object of the present invention to provide proteolytic enzyme compositions capable of digesting connective tissue in a reproducible and predictable manner.

It is another object of the present invention to provide proteolytic enzyme compositions capable of dissociating and isolating viable cells with predictable and reproducible yields and quality.

It is another object of the present invention to provide tissue digestion procedures and associated therapeutic procedures which provide reproducible and predictable results.

It is a further object of the present invention to provide viable and efficacious microvessel cells isolated from fatty tissue mixtures for incorporating on the inner surface of artificial vascular grafts and other medical implants.

SUMMARY OF THE INVENTION

The present invention accomplishes the above objectives by providing proteolytic enzyme compositions capable of predictably and reproducibly digesting physiological connective tissue in a variety of therapeutic and laboratory applications. Further, the present invention provides processes for digesting connective tissue and dissociating cells from the connective tissue, providing efficaciously viable cells in high yield. The viable cells thereby provided have utility in a variety of in vivo and in vitro applications.

The present invention is based upon the discovery that, although neither collagenase nor chymopapain alone is effective to digest tissue, a mixture of collagenase and chymopapain can be used to safely, reproducibly and reliably digest connective tissue formed of a variety of proteins and glycoprotein extracellular matrix material. As a feature of the present invention, compositions of purified collagenase and chymopapain have been found to effectively digest connective tissue and reproducibly dissociate and isolate cells embedded in the tissue, providing the isolated cells in high yield. Moreover, because the isolated cells have been processed with compositions of purified enzymes, the cell suspensions are essentially free of the harmful effects of toxins and unknown unreactive materials, making them highly viable and safe for in vivo use.

More particularly, the present invention provides novel enzyme compositions and associated methodologies useful for hydrolyzing connective tissue in biological systems. The enzyme compositions of the present invention principally comprise a combination of collagenase, in an amount sufficient to hydrolyze collagen in the biological system, and chymopapain in an amount sufficient to hydrolyze chymopapain active tissue in the biological system. Preferably, as a feature of the present invention the collagenase and chymopapain are purified and essentially free of toxic components, such as bacterial DNA and sensitizing antigens, and the collagenase is essentially free of noncollagen specific components.

It is also within the scope of the present invention to provide associated processes utilizing these enzyme compositions of collagenase and chymopapain. These processes effectively hydrolyze connective tissue systems and dissociate cells embedded in the tissue to produce highly efficacious and viable cells in high yield. An exemplary process of the present invention includes enzymatically digesting connective tissue by providing an enzyme composition of collagenase, essentially free of collagen inactive components and toxins and in an amount sufficient to hydrolyze the collagen present in the connective tissue, and chymopapain essentially free of toxins and in an amount sufficient to hydrolyze chymopapain active tissue in the connective tissue. Contacting the enzyme composition with the connective tissue produces a turbid appearing system indicating substantial tissue hydrolysis.

More specifically, a preferred process of the present invention utilizes the above steps to hydrolyze connective tissue associated with fatty tissues in order to dissociate and isolate microvessel cells embedded in the fatty tissue. Advantageously, microvessel cells which form part of the mixture are dissociated from the connective tissue and isolated in higher yield and have improved viability when compared with microvessel cells isolated from tissue hydrolyzed according to prior art procedures which utilize crude collagenase. The higher yield of microvessel cells provided by the processes of the present invention is characterized by the increased number of isolated cells shown to have the expected sizes which are indicative of viable healthy cells.

The increased yield as well as increased viability and integrity of cells isolated according to the processes of the present invention are readily demonstrated by laboratory testing techniques. More particularly, cell counting techniques provide cell size information and information relating to the distribution of cell sizes in a given batch of isolated cells. Similarly, cell viability and efficacy are demonstrated by the degree of cell proliferation activity, which measures the activity of an enzyme present in the viable cells.

The greater viability and number of useful cells isolated according to the teachings of the present invention are particularly important for applications which involve coating the interior wall of synthetic small vessel grafts. This is because the ability of these dissociated microvessel cells to prevent protein deposition and subsequent occlusion is correlated with the total number and the viability of these cells.

Further objects, features, and advantages of the present invention will become apparent to those skilled in the art from a consideration of the following detailed description taken in conjunction with the associated drawings.

DESCRIPTION OF EXEMPLARY EMBODIMENTS

The present invention provides proteolytic enzyme compositions and processes capable of predictably and reproducibly digesting physiological connective tissue in a variety of therapeutic and laboratory applications. These applications range from in vivo therapeutic treatment procedures to techniques which involve dissociating and isolating cells embedded in connective tissue for subsequent laboratory or clinical applications.

The compositions and processes of the present invention are suitable for reproducibly hydrolyzing or digesting a wide variety of collagens, noncollagenous connective tissue proteins, and glycoprotein extracellular matrix materials. Those skilled in the art will appreciate that the ability to hydrolyze a wide range of proteins and protein mixtures makes the teachings of the present invention widely applicable in a number of tissue digestion procedures including those which involve in vivo digestion such as intervertebral discolysis, the treatment of submucous fibrosis, and the treatment of atherosclerotic plaques.

The compositions and processes of the present invention find particular application in cell dissociation procedures including laboratory cell culture methods and related cell isolation techniques. As a feature of the present invention, cells can be effectively and reproducibly isolated from a host of different proteinaceous connective tissues and harvested in higher yield with improved preservation of the cell membranes. Moreover, these cells have better viability and are free of toxins and contaminants, when compared with cells isolated using prior art processes. For this reason, the compositions and processes of the present invention are particularly suitable for isolating microvessel cells embedded in fatty connective tissues for subsequent utility as coatings for implantable small diameter vessel grafts. However, those skilled in the art will recognize that the compositions and processes of the present invention additionally have utility in cell isolation applications including but not limited to isolating pancreatic cells and hepatocytes for transplanting into individuals suffering from pancreatic, liver, or other types of diseases.

More particularly, the enzyme compositions of the present invention include purified collagenase in an amount sufficient to hydrolyze collagen present in the system, and chymopapain in an amount sufficient to hydrolyze chymopapain active tissue in the system. The collagenase and the chymopapain are purified and essentially free of toxic components such as bacterial components and sensitizing antigens. Additionally, the collagenase is free of collagen inactive components.

Preferred exemplary embodiments of the present invention are solutions of collagenase and chymopapain in a physiologically compatible liquid. Suitable physiologically compatible liquids include phosphate buffered saline solutions and similar buffered electrolyte solutions having osmolalities which are compatible with physiological tissue. A particularly suitable commercially available electrolyte solution is Plasmalyte® electrolyte solution available from Baxter-Hyland, having a buffered pH of 7.4 and an osmolarity of 294 mOsmol/L obtained with controlled concentrations of sodium, potassium, magnesium, chloride, acetate, and gluconate ions. As illustrated below, additives such as human serum albumin are preferred in many applications.

Those skilled in the art will appreciate that the concentration or amount of each enzyme present in the solutions will vary with the amount and the type of tissue to be hydrolyzed. The well-known principles of enzyme activity are applicable and basic experimentation involving techniques designed to optimize enzyme concentration and total activity provide necessary information to assure the effective hydrolysis of the amount and type of selected connective tissue. For applications directed toward digesting connective tissue in mixtures of fatty tissue, for example liposuctioned fat, and dissociating cells embedded in the fatty tissue, exemplary compositions of the present invention include a solution of from about 1 nkat/ml to about 500 nkat/ml purified collagenase and from about 0.01 nkat/ml to about 5 nkat/ml purified chymopapain in a suitable pH buffered physiologically compatible liquid containing human serum albumin. The nkat/ml unit is defined as nanomoles of substrate hydrolyzed per second by 1 ml of enzyme solution under the assay condition used. In a preferred embodiment of the present invention, the enzyme composition is a solution of 50 nkat/ml purified collagenase and 0.25 nkat/ml chymopapain in a solution of about 0.4 wt % human serum albumin in Plasmalyte® electrolyte solution.

Most commercial collagenase is derived from the bacterium Clostridium histolyticum and in its crude form differs from batch to batch in hydrolytic activity and purity. Uncontrolled amounts of impurities found in crude collagenase may include contaminating bacterial components, pigment, pyrogens, proteases, and peptidases, including clostripain, trypsin, and caseinase. On the other hand purified collagenase, suitable for use in the compositions of the present invention, is substantially free of pigment, bacterial components, and nonspecific enzyme activity. Crude collagenase is readily available from a number of commercial sources including Sigma Chemical Company of St. Louis, Missouri, and Boehringer Mannheim Biochemicals of Indianapolis, Ind. Commercial sources of crude forms of collagenase are typically packaged in a lyophilized powder form which helps maintain its stability. Alternative sources of collagenase which are substantially free of toxins and collagen inactive compounds include collagenase purified according to the process described in Bond et al. "Purification and Separation of Individual Collagenases of *Clostridium histolyticum* Using Red Dye Ligand Chromatography", *Biochemistry* Vol 23, No. 13, 3077-3091, 1984. By removing non-specific enzyme activities and minimizing or eliminating sensitizing antigens in order to minimize immunogenicity, purified collagenase suitable for use in accordance with the present invention exhibits a batch to batch uniformity in specificity for collagen as well as toxin-free characteristics.

Similarly, chymopapain, a proteolytic enzyme extracted from papaya latex, is commercially available in a dry lyophilized state from a number of sources including Sigma Chemical of St. Louis, MO. Chymopapain is available in crude, partially purified, and more highly purified forms which differ in the amount of papain, lysozyme peptidase A and sensitizing antigens found in the preparation. Chymopapain suitable for use in the present invention is characterized as having essentially no immunogenicity and essentially no toxicity as a result of purification processes. Chymopapain from most commercial sources, which has been purified using known chromatographic purification processes, provides chymopapain suitable in the practice of the present invention. Alternatively, purified chymopapain can be prepared using, for example, the process described in U.S. Pat. No. 4,719,108.

An exemplary tissue system demonstrating the features of the present invention is connective tissue. Generally, connective tissue, which holds cells together, is a complex mixture of collagen, glycoproteins, and mucopolysaccharides. Purified collagenase alone will not effectively hydrolyze all of this extracellular matrix material. However, it has been discovered by the present inventors that by combining purified collagenase with toxin-free chymopapain a wide range of connective tissue systems and biologically derived raw materials can be predictably digested. Moreover, the hydrolyzed tissues and cells isolated during these hydrolysis processes are free of antigenic components which can cause anaphylactic shock if present in cells or tissues implanted or digested in vivo. Accordingly, cells isolated in accordance with the present invention for subsequent implantation do not present toxic health hazards to their recipients. Similarly, the compositions of the present invention can be utilized for in vivo procedures with little risk of anaphylactic shock.

The enzyme compositions of the present invention can be prepared according to processes known in the art. Typically, these processes involve mixing the two enzymes in a selected physiologically compatible liquid such as phosphate buffered normal saline solution or Plasmalyte ® electrolyte solution containing human serum albumin (HSA) and $CaCl_2$. Then lyophilizing the resulting aqueous solution provides a stable dry enzyme preparation which can be reconstituted with deionized water. Preferably, the compositions are reconstituted just prior to their use in order to minimize any degradation that may occur once the enzymes are placed in solution. Similarly, it is preferred that the prepared enzyme compositions are maintained at reduced temperatures in the range of about 4° C. until their use. Alternatively, separate stock solutions of each enzyme, which typically include concentrated forms of the enzyme in a buffered saline solution, can be prepared in advance and stored frozen at about −80° C. Just prior to use, the solutions are thawed, diluted with a suitable physiologically compatible diluent to a desired enzyme activity or concentration, and then combined to form the enzyme composition. Suitable diluents include aqueous based solutions buffered to a pH of about 7.4 and having a physiologically compatible osmolarity.

It is additionally within the scope of the present invention to utilize these compositions in processes for digesting connective tissue. Thus, the processes of the present invention broadly include providing a composition of the present invention and causing the composition to contact selected tissue for a length of time and at a temperature sufficient to substantially hydrolyze the tissue. These procedures more particularly include administering an enzyme composition of the present invention to a human or animal for the treatment of burns or ulcers, for intervertebral discolysis, for assisting in ophthalmic surgery, for the treatment of submucous fibrosis, for the treatment of Peyronie's disease, for the local enzymatic treatment of atherosclerotic plaques, and in the treatment and prevention of the development of familial amyloidotic polyneuropathy (FAP).

Preferred exemplary processes in accordance with the teachings of the present invention include digesting connective tissue for the purpose of dissociating and isolating cells embedded in the connective tissue. When used in accordance with processes known in the art for dissociating and isolating cells, the compositions of the present invention provide highly viable cells which are particularly useful for gene therapy and transplanting into humans or animals for therapeutic purposes. For example, pancreatic cells can be isolated from donor pancreases and transplanted into humans or animals for purposes of treating pancreatic related diseases. Additionally, hepatocytes can be isolated from liver in accordance with known procedures utilizing compositions of the present invention. Similarly, skin cells, neurons, and tumor cells can be dissociated from connective tissue in which they are embedded, and used for a variety of therapeutic or investigative purposes.

A most preferred process of the present invention includes providing an appropriate enzyme composition of the present invention and contacting the enzyme composition with fatty tissue such as liposuctioned fat for a length of time and at a temperature sufficient to substantially hydrolyze the connective tissue and to dissociate microvessel cells embedded in the fatty raw material. For purposes of dissociating and isolating cells embedded in liposuctioned fat, an exemplary preferred process for digesting tissue includes the steps of providing an enzyme composition of a Plasmalyte ® electrolyte solution of about 50 nkat/ml purified collagenase, about 0.25 nkat/ml chymopapain and about 0.4 wt % human serum albumin. Then, the enzyme composition is combined with a liposuctioned fatty tissue mixture at a ratio of 1 ml of enzyme composition to 1 g of the mixture and the combination is incubated at about 37° C. while shaking until the combination becomes turbid. At this point sufficient tissue hydrolysis is achieved.

Further separating viable microvessel cells from the incubated combination can be accomplished by centrifuging the incubated combination until adipocytes and a supernatant are separated from the microvessel cells, which form as a pellet. The microvessel cell pellets are recovered from the separated combination by pipeting off the adipocytes and supernatants. This provides isolated cells in the form of pellet. Preferred exemplary processes further include rinsing the cell pellets with a physiologically compatible liquid and then centrifuging the rinsed cell pellet prior to the evaluation and use of the cells.

Fatty tissue derived from liposuction which are subject to digestion in accordance with the present invention should be substantially homogeneous and without apparent large pieces of fat. Accordingly, nonhomogeneous appearing liposuctioned fatty tissue should be minced in a tissue mincer prior to further treatment. Additionally, the liposuctioned fatty tissue is preferably rinsed with a suitable physiologically compatible rinsing solution in order to remove visual blood contaminants including clotted blood. Suitable rinsing solutions include those having pH ranges and osmolarity ranges which are compatible with cellular material such as phosphate buffered saline and Plasmalyte ® electrolyte solution. A preferred method for rinsing the mixture involves transferring the liposuctioned fatty tissue into a sieve-tissue grinder cup and adding phosphate buffered saline solution to the mixture while stirring. Excess liquids and blood contaminants are removed by the rinsing and sieving process. The homogenized and rinsed liposuction fatty mixture is then prepared for the above-described digestion and microvessel cell dissociation procedures.

As generally mentioned above, microvessel cells isolated from liposuctioned fatty tissues in accordance with the teachings of the present invention are isolated in higher yields and have greater viability than microvessel cells isolated by prior art processes. Moreover, since the enzyme compositions used in the processes of the present invention are free of toxins, in the event that isolated cells are implanted for therapeutic purposes or are subjected to other in vivo uses, any residual cotransplanted enzyme composition will not pose the threat of an anaphylactic or other adverse response.

Figure 3A:
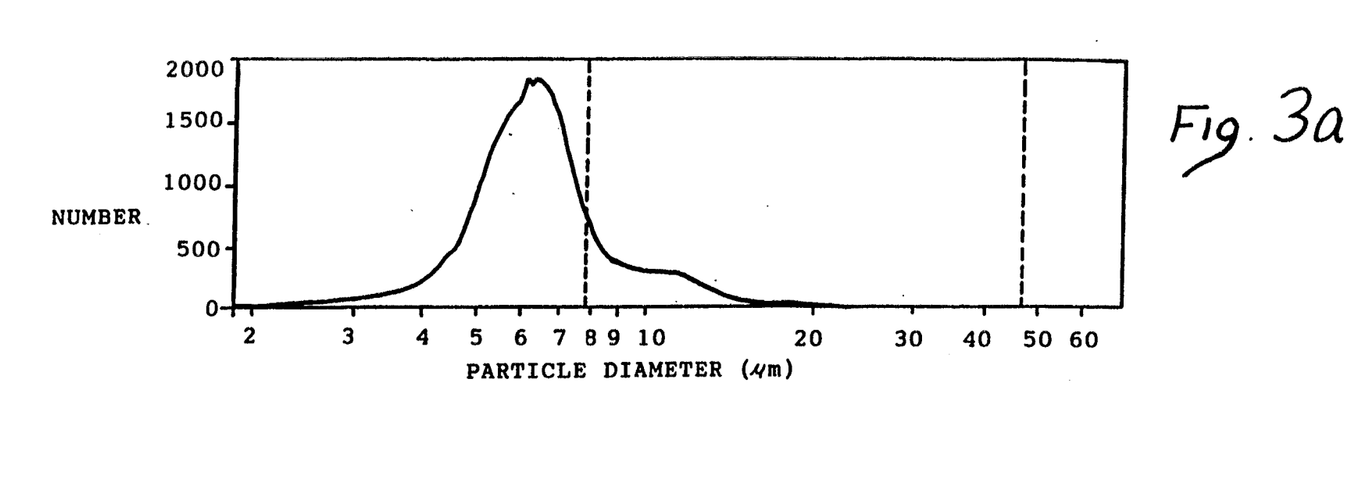
FIG. 3a illustrates the particle size distribution of cells isolated utilizing prior art enzyme compositions.
Figure 3B:
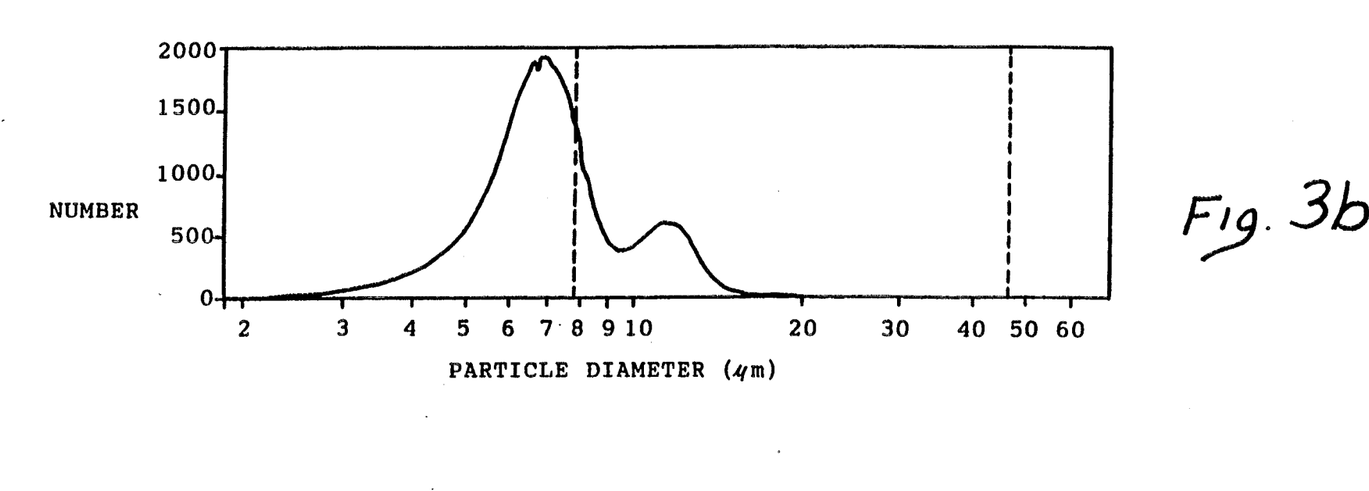
FIG. 3b illustrates the particle size distribution of cells isolated utilizing enzyme compositions of the present invention.

The superior physical and functional characteristics of the cells isolated according to the process of the present invention are demonstrated by the higher yield of cells having expected sizes as determined by known cell counting methods. Other indicators of the superior results obtained by the present invention include the improved adhesion capabilities and cell proliferation activities of the isolated cells. The improved ability of cells to adhere to surfaces and to freely proliferate demonstrates their improved viability. Similarly, since intact and viable microvessel cells are larger than 7.78μ, a higher yield of these larger cells, as produced by the present invention, is an indicator of a highly safe and efficacious process. An exemplary cell size distribution profile of cells isolated according to prior art procedures utilizing prior art enzyme compositions is illustrated in FIG. 3a. A comparison size distribution profile of cells isolated according to the present invention is illustrated in FIG. 3b. A simple visual observation of these two profiles clearly demonstrates that when compared with prior art procedures the processes of the present invention provide a higher yield of material having large particle diameters. The large particle diameter material is known to be highly viable metabolically active cells. In contrast, small particle size materials include cellular material and tissue debris having little therapeutic usefulness.

As described in more detail in the examples which follow, when compared with cells isolated by prior art processes utilizing crude collagenase, the process of the present invention provides greater numbers of microvessel cells over 7.78μ in size as demonstrated by Coulter Counter analyses. For example, digesting fatty tissue utilizing a prior art enzyme composition of 4 mg/ml crude collagenase in a solution of 0.4 wt % human serum albumin in Plasmalyte ® electrolyte solution provides an average of 7944 cells over 7.78μ in size. In contrast, a comparable procedure utilizing the present invention enzyme composition of purified collagenase at 51 nkat/ml of collagenase and 0.33 nkat/ml chymopapain in Plasmalyte ® electrolyte solution provides an average of 13,525 microvessel cells over 7.78μ in size. These exemplary results of Coulter Counter analyses demonstrate the higher yield and larger size distribution of cells isolated according to the process of the present invention.

Similarly, cell adhesion studies performed by incubating a fixed number of cells on cell culture plates having a coating of cell adhesion molecules, washing the plates to remove unattached cells and then visualizing the density of attached cells further demonstrate the improved preservation and integrity of cells isolated according to the teachings of the present invention. As detailed in the examples which follow, microvessel cells isolated from connective tissue utilizing solutions of purified collagenase and chymopapain in accordance with the teachings of the present invention produce densely covered areas of attached cells on the cell culture plates. As known in the art this is indicative of highly viable cells with active surface receptors for adhesion materials being preserved through the present invention. Finally, cell proliferation studies of cells isolated according to the present invention further demonstrate their enhanced integrity. The following examples clearly show that cells which have been isolated according to the present invention and then allowed to proliferate have a higher enzyme activity, an indication of the presence of more metabolically active cells, than those isolated according to prior art procedures. These results clearly demonstrate that cells treated in accordance with the teachings of the present invention have greater functional integrity than comparably treated cells using prior art enzyme compositions and methodologies.

The resultant superior physical and functional characteristics of microvessel cells isolated according to the present invention make them particularly useful as coatings for the interior walls of small diameter artificial vessel grafts. These grafts are typically fabricated of polymeric materials, such as expanded polytetrafluoroethylene, and implanted in humans and other mammals as artificial blood vessels. When deposited on the interior surface of these artificial grafts according to methods known in the art, the increased population and better viability of the microvessel cells produced through the present invention make it easier for the cells to effectively adhere to the interior walls of the graft with thorough coverage and to maintain their functional integrity. The high viability and functional ability of these cells provides a graft surface that is less prone to protein and related cellular depositions. Accordingly, grafts treated according to the teachings of the present invention are less susceptible to functional failure such as occlusion caused by protein and cellular deposits.

The invention will be better understood by reference to the following nonlimiting examples which illustrate the use of exemplary enzyme compositions of the present invention in processes for digesting fatty tissue derived from liposuction procedures. In these examples the activity of collagenase is expressed as nkat/ml of enzyme composition as determined by assay using FALGPA, furylacryloyl Leu-Gly-Pro-Ala synthetic substrate. The activity of chymopapain was determined by assay using BAPNA, Benzoyl-L-arginine-p-nitroanilide synthetic substrate.

The following example demonstrates the superior characteristics of cells isolated according to the present invention.

EXAMPLE 1

A control crude collagenase enzyme solution containing 4 mg/ml collagenase and 0.4 wt % human serum albumin in Plasmalyte ® electrolyte solution was centrifuged at 20,000 rpm in a Dupont rotor ss-34, with a Dupont Centrifuge model RC285, at 4° C. for 20 minutes, and then sterile filtered through a 0.45 micron filter. Collagenase/chymopapain solutions were prepared by diluting stock solutions of purified collagenase and chymopapain stored at −80° C. in Plasmalyte® electrolyte solution containing 0.4 wt % human serum albumin. Liposuctioned fatty tissue was minced at a ratio of 1.2 g. tissue to 1 ml of enzyme solution, and rinsed in a 100 ml sieve-tissue grinder cup by pouring 40 ml. of PBS over 30 g. of tissue while stirring. Excess liquid was sieved and removed along with blood contaminants.

Nine (9) g. tissue samples were added to sterile Erlenmeyer flasks and 9 ml. of the enzyme solution was then added to each flask. The flasks were placed into sterile plastic bags and moved to a 37° C. water bath shaker. After shaking the flasks at 100 cycles/min. for 20 minutes, an aqueous portion of digested tissue appeared as a turbid layer. The contents of each flask were transferred to centrifuge tubes and centrifuged at 700 G for 7 minutes at room temperature.

Adipocytes were observed to separate from the microvessel cells and form a layer on top of each tube. Additionally, a liquid supernatant appeared above the dissociated cells, which formed as a pellet at the bottom of each tube. The adipocytes and supernatant were pipetted off from the tubes and the dissociated and isolated cells were resuspended in PBS containing 0.1 wt % human serum albumin. The resuspended cells were centrifuged again at 700 G for 4 minutes at room temperature, collected from the bottom of the tube and resuspended in Plasmalyte® electrolyte solution containing 20% human serum.

In order to evaluate the size distribution of the cells, 0.5 ml of cells isolated by each enzyme composition were separately added to Coulter Multisizer AccuComp cell counting vials, each containing 19.5 ml of Isoton counting fluid. The cell concentration and size distribution of the isolated cells in each vial were determined according to directions provided by the manufacturer. The results of the size distribution experiments for each sample enzyme composition are tabulated in Table I.

TABLE I

| SAMPLE ID NUMBER | SAMPLE SOLUTIONS | AVERAGE # OF COUNTED CELLS >7.78μ | # OF CELLS PER GRAM TISSUE >7.78μ |
|---|---|---|---|
| A | crude collagenase 4 mg/ml (control) | 7944 | $0.718 \times 10^6$ |
| B | 43 nkat/ml collagenase, lot A 0.22 nkat/ml chymopapain | 8128 | $0.721 \times 10^6$ |
| C | 51 nkat/ml collagenase, lot A 0.22 nkat/ml chymopapain | 9606 | $0.848 \times 10^6$ |
| D | 43 nkat/ml collagenase, lot A 0.33 nkat/ml chymopapain | 9119 | $0.811 \times 10^6$ |
| E | 51 nkat/ml collagenase, lot A 0.33 nkat/ml chymopapain | 10858 | $0.971 \times 10^6$ |
| F | 43 nkat/ml collagenase, lot B 0.22 nkat/ml chymopapain | 10476 | $0.940 \times 10^6$ |
| G | 51 nkat/ml collagenase, lot B 0.22 nkat/ml chymopapain | 8710 | $0.778 \times 10^6$ |
| H | 43 nkat/ml collagenase, lot B 0.33 nkat/ml chymopapain | 11257 | $1.01 \times 10^6$ |
| I | 51 nkat/ml collagenase, lot B 0.33 nkat/ml chymopapain | 13525 | $1.21 \times 10^6$ |

The data in Table I show that when Sample A, the control, was used to isolate cells from liposuctioned fat, only 7,944 cells over 7.78 microns in size were counted. By contrast, when the enzyme compositions of the present invention, shown as samples B–I, were used to isolate cells from liposuctioned fat, from 8,128 to 13,525 cells sized over 7.78 microns were isolated. Additionally, the number of cells per gram of liposuctioned fatty tissue isolated with the control (Sample A) is only $0.718 \times 10^6$ compared with up to $1.21 \times 10^6$ cells per gram of tissue (Sample I) using the enzyme compositions of the present invention. It can be seen that, relative to prior art compositions, the use of the enzyme compositions of the present invention results in greater cell concentrations and cell size distributions having higher numbers of large cells.

The following example illustrates the cell integrity of cells isolated in accordance with the present invention.

EXAMPLE 2

Cell adhesion experiments were performed upon each of the cell isolates of Example I. The experimental protocol consisted of testing the ability of the isolated microvessel cells to adhere to extracellular matrix (ECM) treated surfaces. In each trial an equal number of cells having sizes larger than 7.78 microns isolated using each sample enzyme composition were incubated in culture plates treated with ProNectinF, a genetically engineered ECM, or fibronectin, a natural ECM. After 2 hrs, each plate was washed to removed unattached cells and then stained with amido black to visually reveal the attached cells. Microscopic visualization and photomicrographs of the stained plates were evaluated and clearly indicated that a much higher cell density was obtained on plates having adhered cells which had been isolated from enzyme compositions of the present invention containing purified collagenase and chymopapain.

The following example illustrates the greater viability of cells isolated in accordance with the present invention.

EXAMPLE 3

Figure 1:
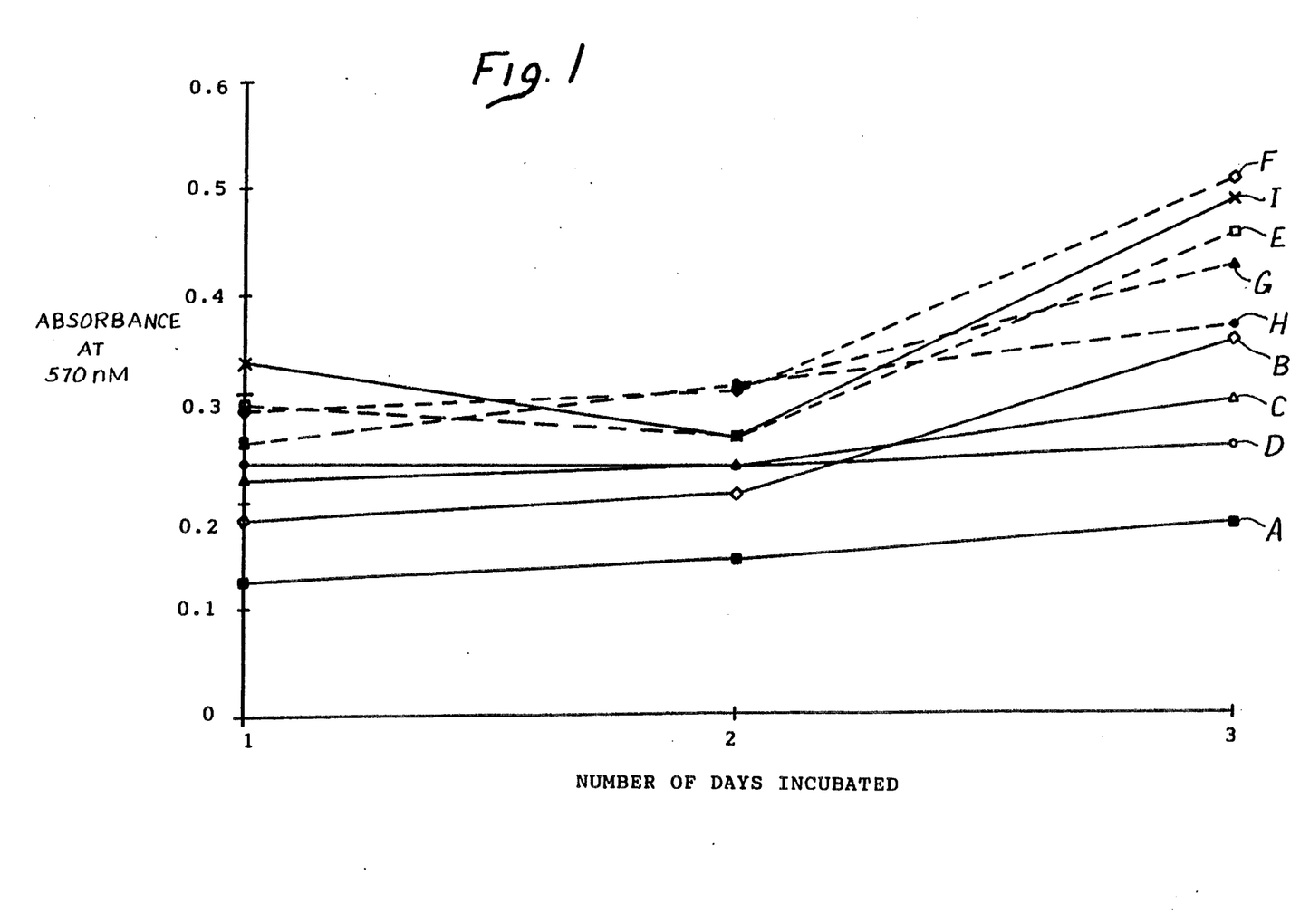
FIG. 1 is a plot of the absorbance at 570 nm vs time of treated microvessel cells proliferated over a period of 3 days and demonstrates the higher viability of microvessel cells isolated according to the present invention.

Individual samples of an equal volume of microvessel cell suspensions isolated by each enzyme composition of Example 1 were allowed to proliferate in growth medium. Then the metabolic activity of the cells was measured by allowing the cells to convert a substrate to a colored product having an absorption maximum at 570 nm. By measuring the absorption of each proliferation sample at 570 nm, the relative degree of proliferation was determined for each set of isolated microvessel cells. The results of this comparative test are represented in the graph of FIG. 1, which illustrates the absorbance at 570 nm, of each group of proliferated microvessel cells over a 3 day period. The plots of absorbance vs. time identified in FIG. 1 as A–I correspond to cells isolated by Samples A–I identified in Table I.

As shown in FIG. 1, the cells isolated by digestion with the prior art crude collagenase composition had the least amount of proliferated cells. In contrast, the microvessel cells isolated from compositions of purified collagenase and chymopapain in accordance with the present invention showed relatively increased degrees of proliferation.

These comparative test results of the experiments directed toward determining the number of cells larger than 7.78µ, size distribution, cell adhesion characteristics, and proliferation capabilities of cell isolates produced through the teachings of the present invention versus those of the prior art clearly demonstrate the superior properties of microvessel cells isolated using the present invention. Cells isolated using the enzyme compositions of the present invention have greater viability and integrity and an improved ability to anchor themselves to substrates.

EXAMPLE 4

The procedure of Example 1 was followed using a different fatty tissue sample and varying the enzyme compositions to some extent. The results are shown in Table II.

TABLE II

| SAMPLE ID NUMBER | SAMPLE SOLUTIONS | AVERAGE # OF COUNTED CELLS >7.78µ | # OF CELLS PER GRAM TISSUE >7.78µ |
|---|---|---|---|
| A | crude collagenase | 7947 | $0.707 \times 10^6$ |
| B | crude collagenase | 6802 | $0.636 \times 10^6$ |
| C | 51 nkat/ml collagenase, lot C 0.22 nkat/ml chymopapain | 8789 | $0.787 \times 10^6$ |
| D | 51 nkat/ml collagenase, lot A 0.22 nkat/ml chymopapain | 8448 | $0.760 \times 10^6$ |
| E | 51 nkat/ml collagenase, lot C 0.44 nkat/ml chymopapain | 10552 | $0.937 \times 10^6$ |
| F | 51 nkat/ml collagenase, lot A 0.44 nkat/ml chymopapain | 9224 | $0.816 \times 10^6$ |

The results are similar to those shown in Table I, indicating that beneficial results can be obtained using a wide variety of enzyme compositions.

Optical microscopic examination of stained cells attached to culture plates as a result of the adhesion experiments described in Example 2 showed a much higher cell density on plates having adhered cells isolated from the enzyme compositions of the present invention relative to the crude prior art compositions.

Figure 2:
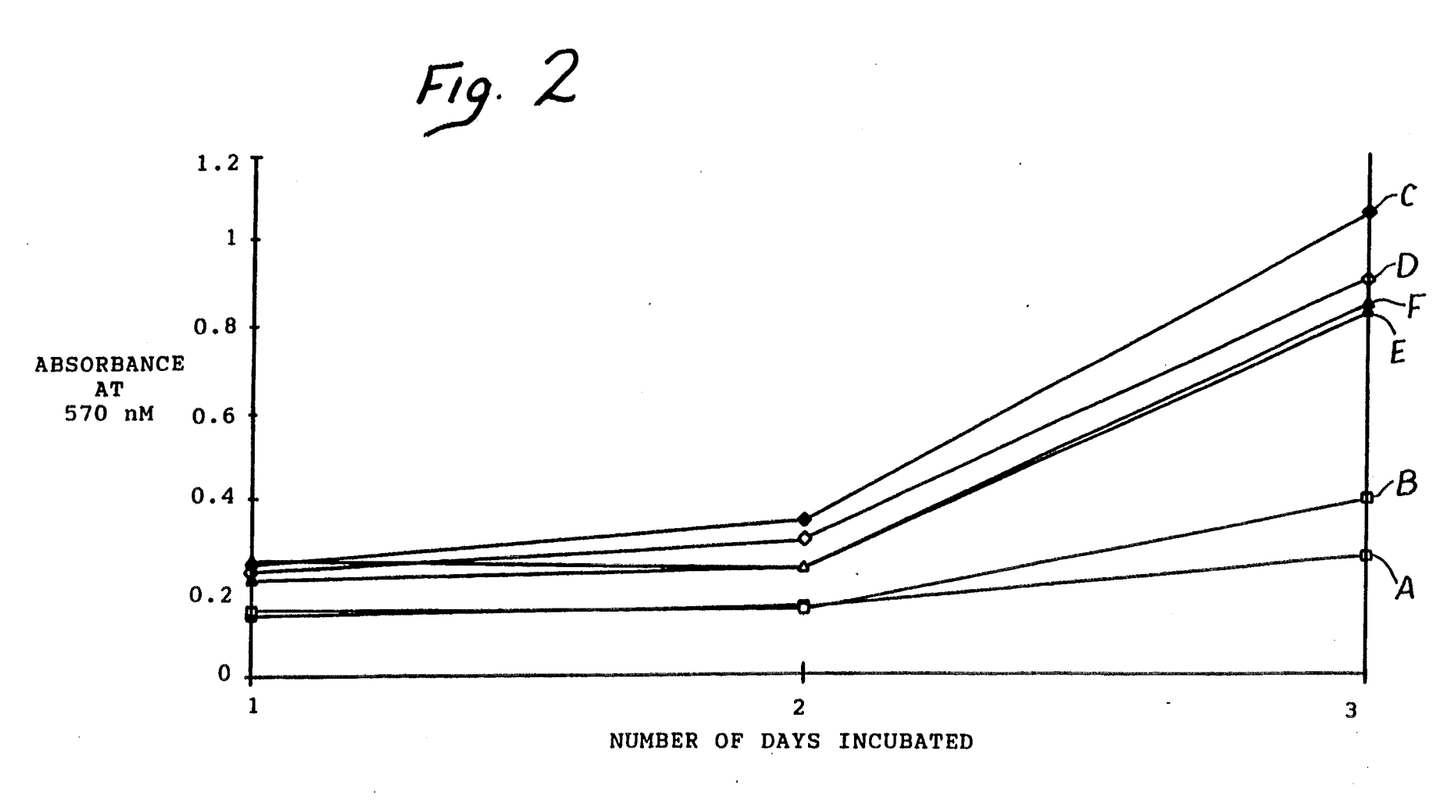
FIG. 2 is a plot of the absorbance at 570 nm vs time of treated microvessel cells proliferated over a period of 3 days and demonstrates the higher viability of microvessel cells isolated according to the present invention.

Cell proliferation tests of the cell isolates as described in Example 3 are shown in FIG. 2, where the absorbance at 570 nm of substrate treated microvessel cells isolated by the various enzyme compositions over a 3 day period is illustrated. The cells isolated by digesting the fatty mixture with the crude collagenase composition had the least amount of proliferated cells. In contrast, the microvessel cells isolated with the compositions of the present invention showed increased degrees of proliferation.

These experimental results further demonstrate the superior properties of microvessel cells isolated using purified collagenase and chymopapain as disclosed by the teachings of the present invention. These results also demonstrated that any purified collagenase lot was effective when their activities were adjusted to the required level.

Having thus described preferred exemplary embodiments of the present invention, it should be noted by those skilled in the art that the disclosures herein are exemplary only and that alternatives, adaptations, and modifications may be made within the scope of the present invention. Accordingly, the present invention is not limited to the specific embodiments illustrated herein.

We claim:

1. An enzyme composition useful for hydrolyzing connective tissue, said composition comprising:
an aqueous mixture of collagenase having an activity of about 43 nkat/ml to about 51 nkat/ml, and chymopapain having an activity of about 0.22 nkat/ml to about 0.44 nkat/ml, in a physiologically compatible electrolyte solution buffered to a pH of about 7.0 to 7.4, wherein the activity of collagenase in nkat/ml is defined as the number of nanomoles of furylacryloyl Leu-Gly-Pro-Ala synthetic substrate (FALGPA) hydrolyzed per second by 1 ml of collagenase solution and the activity of chymopapain in nkat/ml is defined as the number of nanomoles of Benzoyl-L-arginine-p-nitroanilide synthetic substrate (BAPNA) hydrolyzed per second by 1 ml of chymopapain solution, said collagenase being essentially free of toxins and non-collagen active components and said chymopapain being essentially free of toxins.

2. The enzyme composition of claim 1 wherein said electrolyte solution is a phosphate buffered saline solution.

3. The enzyme composition of claim 1 wherein said electrolyte solution is an aqueous solution of sodium, potassium, magnesium, chloride, acetate, and gluconate ions buffered to a pH of 7.4, and having an osmolarity of 294 mOsmol/L.

4. The enzyme composition of claim 1 further comprising about 0.4 wt % human serum albumin.

* * * * *